United States Patent
Eibl

(10) Patent No.: US 7,592,469 B2
(45) Date of Patent: Sep. 22, 2009

(54) LIPID-ANALOGOUS PHOSPHORIC ACID TRIESTERS

(75) Inventor: Hansjoerg Eibl, Bovenden (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 352 days.

(21) Appl. No.: 10/529,889

(22) PCT Filed: Oct. 1, 2003

(86) PCT No.: PCT/EP03/10870

§ 371 (c)(1),
(2), (4) Date: Apr. 1, 2005

(87) PCT Pub. No.: WO2004/031199

PCT Pub. Date: Apr. 15, 2004

(65) Prior Publication Data

US 2006/0039963 A1   Feb. 23, 2006

(30) Foreign Application Priority Data

Oct. 1, 2002   (DE) .............................. 102 45 909

(51) Int. Cl.
*C07F 9/02* (2006.01)
*C07F 9/06* (2006.01)
*A61K 9/127* (2006.01)

(52) U.S. Cl. .................... 554/78; 514/75; 424/450
(58) Field of Classification Search ................. 424/450; 554/78
See application file for complete search history.

(56) References Cited

U.S. PATENT DOCUMENTS

| 5,651,981 A | 7/1997 | Ashley et al. |
| 5,855,910 A | 1/1999 | Ashley et al. |
| 5,891,714 A | 4/1999 | Ashley et al. |

FOREIGN PATENT DOCUMENTS

| DE | 196 22 224 A | 8/1997 |
| WO | WO 95/01163 A | 1/1995 |

OTHER PUBLICATIONS

Database CA 'Online! Chemical Abstracts Services, Cremlyn et al., "Studies of organophosphorochloridates. Reactions of cholesteryl phosphorochloridates with alcohols", Database accession No. 86:121620, & Phosphorus and the Related Group V Elements, 1976, vol. 6, No. 3-4, pp. 201-205.
Murakami et al., "An Efficient Synthesis of Unsymmetrical Optically Active Phosphatidyl Glycerol", J. Org. Chem., vol. 64, 1999, pp. 648-651.
Keana et al., "A Short, Flexible Route to Symmetrically and Unsymmetrically Substituted Diphosphatidylglycerols (Cardiolipins)", J. Org. Chem., vol. 51, No. 12, 1986, pp. 2297-2299.
Bruzik et al., "General Method for the Synthesis of Glycerophospholipids", J. Org. Chem., vol. 51, No. 12, 1986, pp. 2368-2370.
McDonald et al., "O-Ethylphosphatidylcholine: A Metabolizable Cationic Phospholipid Which is a Serum-Compatible DNA Transfection Agent", Journal of Pharmaceutical Sciences, American Pharmaceutical Association, vol. 88, No. 9, Sep. 1999, pp. 896-904.

*Primary Examiner*—Sreeni Padmanabhan
*Assistant Examiner*—Sahar Javanmard
(74) *Attorney, Agent, or Firm*—Rothwell, Figg, Ernst & Manbeck p.c.

(57) ABSTRACT

The present invention relates to novel phosphoric triesters which comprise apolar lipid structures.

10 Claims, No Drawings

LIPID-ANALOGOUS PHOSPHORIC ACID TRIESTERS

CROSS REFERENCE TO RELATED APPLICATION

This application is a 35 USC § 371 National Phase Entry Application from PCT/EP2003/010870, filed Oct. 1, 2003, and designating the United States.

The present invention relates to novel phosphoric triesters which comprise apolar lipid structures.

These triesters can be used in particular as liposome constituents.

One aspect of the invention is a compound of the formula (I)

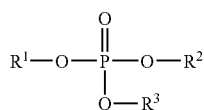

in which $R^1$ is a residue selected from cholesterol, diacylglycerols, dialkylglycerols, acylalkylglycerols, ceramides, primary or secondary alcohols having 12 to 24 C atoms or acylglycerobenzyl ethers, $R^2$ is a residue selected from ethanolamine, N-methylethanolamine, propanolamine, choline, glycerol, oligoglycerols, glycoglycerols or serine, each of which may optionally comprise protective groups, and $R^3$ is a radical selected from $C_1$-$C_8$-alkyl or $C_1$-$C_8$-alkenyl or has the meaning of $R^2$.

The compounds of the invention are lipid-analogous phosphoric triesters, in particular phosphoric triesters having multiple hydroxyl groups per phosphorus atom, in particular at least two hydroxyl groups per phosphorus atom, more preferably at least three hydroxyl groups per phosphorus atom and even more preferably at least four hydroxyl groups per phosphorus atom.

The phosphoric triesters of the invention comprise a residue $R^1$ which comprises an apolar lipid structure. Suitable structures for $R^1$ are in particular cholesterol residues, so that preferred phosphoric triesters are cholesteryl compounds.

A further preferred residue for $R^1$ is diacylglycerol, where the acyl groups each comprise independently preferably 12 to 28, in particular 13 to 27 and more preferably 14 to 26 carbon atoms. The acyl radicals may be saturated or mono- or poly-, in particular di- or triunsaturated radicals. Acylglycerols which comprise unsaturated fatty acid residues such as, for example, residues of oleic acid, linoleic acid or linolenic acid are particularly preferred.

The residue $R^1$ may additionally according to the invention be a dialkylglycerol residue, wherein the alkyl radicals each independently of one another preferably have 1 to 28, in particular 12 to 26, even more preferably 14 to 24 carbon atoms. The alkyl radicals in the dialkylglycerol residue may be saturated or mono- or poly-, in particular di- or triunsaturated. Preferred radicals are (Z)-9-octadecenyl-, (Z.Z.)-9.12-octadecanedienyl-, (Z.Z.Z)-9.12.15-octadecanetrienyl, and lipophilic basic structures with a pharmaceutical effect, such as 1-octadecyl-2-methyl-sn-glycerol.

$R^1$ may further be a ceramide residue. Ceramides are endogenous lipophilic amides which are to be found in particular bound in the cerebral matter and in the myelin of the CNS and have the general formula (IV)

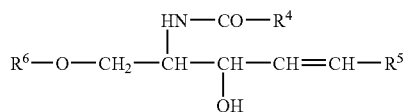

where $R^4$ is a long-chain fatty acid residue, in particular a fatty acid residue having 12 to 28 C atoms, $R^5$ is a long-chain alkyl radical, in particular an alkyl radical having 12 to 28 C atoms and $R^6$ is H.

$R^1$ may further be a residue of a primary or secondary alcohol having 12 to 24 carbon atoms, in particular 13 to 22 carbon atoms, where the alcohols may be saturated or mono- or polyunsaturated.

$R^1$ may further be an acylglycerobenzyl ether residue, it being possible to employ such compounds in particular as starting materials for synthesizing lysophospholipids.

The residue $R^1$ may be present in the compounds of the invention in enantiopure form or as racemic mixture.

$R^2$ can be all the residues occurring in natural phospholipids and sphingomyelins. $R^2$ is in particular an ethanolamine residue, an N-methylethanolamine residue or a propanolamine residue, where the residues are provided where appropriate with suitable protective groups, for example BOC. $R^2$ may further be a choline residue. $R^2$ is preferably —$CH_2$—$CH_2$—$N^+$ $(CH_3)_3$. $R^2$ may further be a glycerol residue (—$CH_2$—CH(OH)—$CH_2$(OH)) and be an oligoglycerol, in particular a di- or triglycerol residue. Further suitable $R^2$ residues are glycoglycerols, and serine residues. The glycerol and serine residues may also where appropriate be provided with suitable protective groups.

$R^3$ is a radical selected from $C_1$-$C_8$-alkyl or $C_1$-$C_8$-alkenyl or may have one of the meanings indicated above for $R^2$. If $R^3$ has one of the meanings indicated for $R^2$, it is possible to form highly biologically active structures which, as novel cationic lipids, have great importance. Such cationic lipids can be employed for example for gene transfection.

$R^3$ may, however, also have only a temporary character, that is to say assume the function of a protective group which is detached again later. In this case, $R^3$ is preferably methyl, ethyl, allyl or propyl.

The compounds of the invention are very stable between pH 3 and pH 8 and can be used in particular as liposome constituents.

The invention further relates to a process for preparing a compound according to formula (I), which is characterized in that a compound of the formula (II) is esterified with a compound of the formula (III) HO—$R^3$.

The compounds are derived from phospholipids and are produced for example from

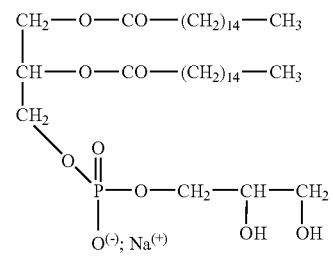

by esterification of the phosphoric diester with glycerol:

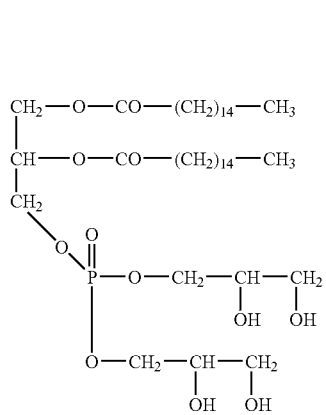

Cholesterol derivatives can also be obtained correspondingly

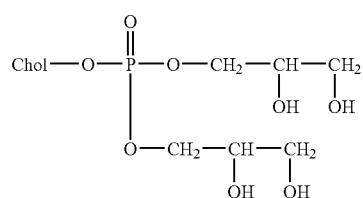

These compounds can be prepared in various embodiments. They may also comprise oligoglycerols, e.g. for example glyceroglycerol, diglyceroglycerol or triglyceroglycerol in place of glycerol. Diagrammatically, for example, cholesterol-phospho-monoglycerol-triglyceroglycerol has the following structural formula:

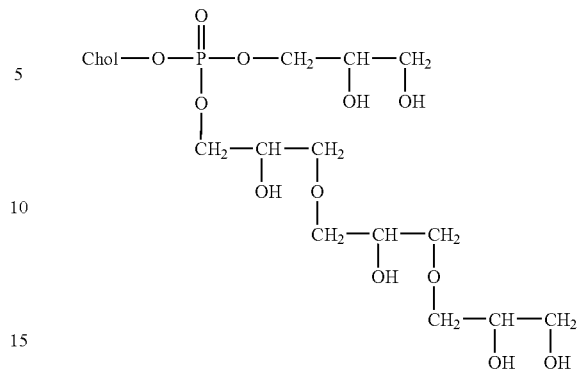

The compounds of the invention are particularly suitable for preparing liposomes and as liposome constituents. They confer particular properties on liposomes, e.g. long circulation times in the blood, targeted enrichment in the liver or else almost exclusive uptake in the spleen. It is also possible with the aid of the phosphoric triesters of the invention to form liposomes with novel properties, which have high serum stability, have long circulation times and accumulate exclusively in the spleen. Long circulation times are, however, also particularly important because the structures then do not, like known liposomes, accumulate in the liver but may hit other targets such as, for example, the spleen or, particularly importantly, be taken up by tumor cells. The compounds of the invention can therefore also be employed for the treatment of cancers.

The invention further relates to a novel synthetic route using the phosphoric triesters of the invention as intermediate. A particular advantage of the synthetic route of the invention is that the reaction direction (a) used in earlier syntheses is avoided, and according to (b) the important compound 1.2-dioleyl-sn-glycero-3-phosphoglycerol or corresponding compounds are liberated under neutral conditions:

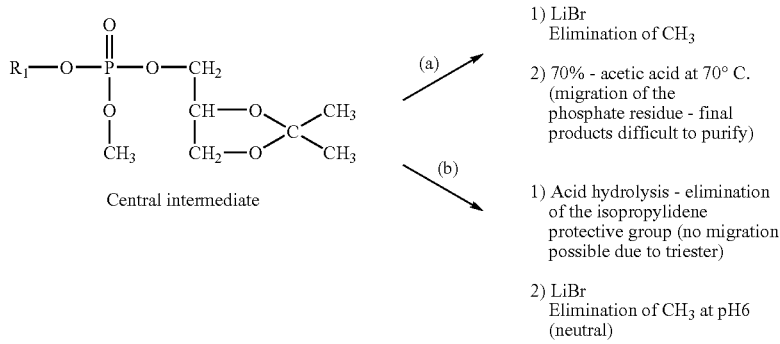

$R_1$ = 1.2-dioleoyl-sn-glycerol

A substantial advantage of the novel management of the synthesis is the possibility of advancing apolar intermediates as far as possible in the synthesis, so that polar structures are introduced only at the end of the process. This is illustrated below in an example. Cardiolipins and analogous compounds are complicated structures which can be obtained only with great difficulty by synthesis in kg quantities. However, with the aid of our novel synthetic strategy, this is easily possible.

Cardiolipin

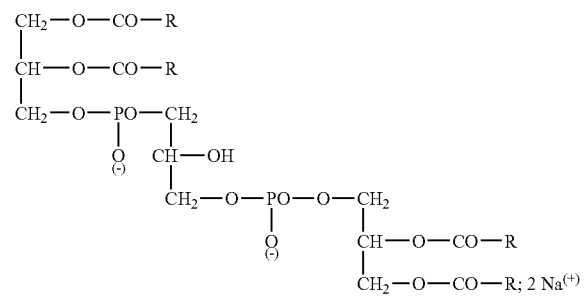

The synthesis is described for the example of R=palmitic acid. The starting material is 1.2-dipalmitoyl-sn-glycerol which is converted with phosphorus oxychloride in THF with triethylamine as base in the usual manner into 1.2-dipalmitoyl-sn-glycero-3-phosphoric dichloride:

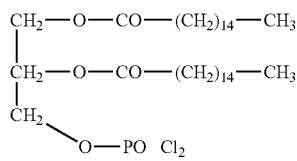

Building Block I

The simple route for synthesizing cardiolipin, direct reaction with 2-benzylglycerol, unfortunately leads to predominant formation of the corresponding phospholane and is not practicable:

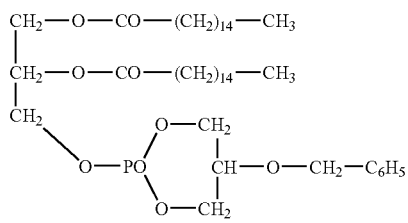

It is therefore necessary to use building block II, a protected glycerol derivative:

Building Block II

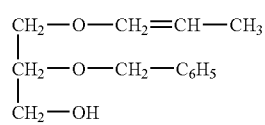

Linkage of building block I with building block II in THF with triethylamine then leads to building block III:

Building Block III

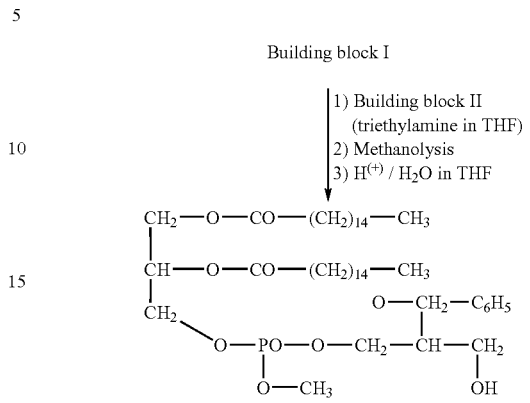

Building block III can then be reacted with building block I in the usual way to give the direct precursor of cardiolipin, which is then converted by

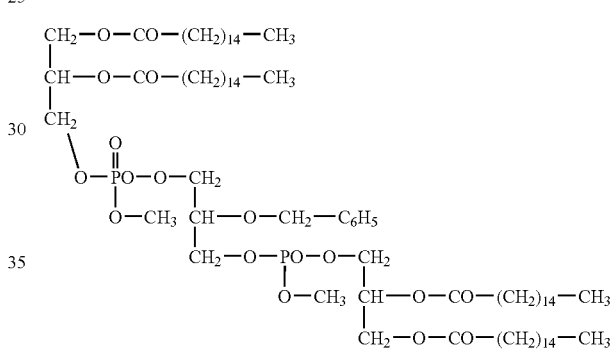

methanolysis into the dimethyl ester. The hydroxyl group on the middle glycerol is then liberated by catalytic hydrogenolysis. The methyl groups are removed by LiBr at neutral pH—the final product is cardiolipin.

The description is illustrated further by the following examples.

EXAMPLE 1

1) Cholesteryl-phospho-diglycerol
   $C_{33}H_{59}O_8P$ (MW 614.801)
2) Cholesteryl-phospho-glycerol-glyceroglycerol
   $C_{36}H65O_{10}P$ (MW 688.880)
3) Cholesteryl-phospho-di-glycoglycerol
   $C_{37}H_{67}O_{10}P$ (MW 702.907)
4) 1.2-Dimyristoyl-sn-glycero-3-phospho-diglycerol
   $C_{37}H_{73}O_{12}P$ (MW 740.953)
5) 1.2-Dipalmitoyl-sn-glycero-3-phospho-diglycerol
   $C_{41}H_{81}O_{12}P$ (MW 797.061)
6) 1.2-Distearoyl-sn-glycero-3-phospho-diglycerol
   $C_{45}H_{89}O_{12}P$ (MW 853.169)
7) 1.2-Dioleoyl-sn-glycero-3-phospho-diglycerol
   $C_{45}H_{85}O_{12}P$ (MW 849.137)
8) 1.2-Dioleoyl-sn-glycero-3-phospho-di-glycoglycerol
   $C_{49}H_{93}O_{14}P$ (MW 937.243)
9) 1.2-Dioleoyl-sn-glycero-3-phospho-di-glyceroglycerol
   $C_{51}H_{97}O_{16}P$ (MW 997.295)

EXAMPLE 2

1) $R_1$: 1.2.-dimyristoyl-glycerol
   $R_2$: choline
   $R_3$: glycerol $$CH_2-O-CO-(CH_2)_{12}-CH_3$$
$$CH-O-CO-(CH_2)_{12}-CH_3$$
$$CH_2\diagdown$$
$$O-\overset{O}{\underset{\|}{P}}-O-CH_2-CH_2-N(CH_3)_3^{(+)}; Cl^{(-)}$$
$$O-CH_2-CH-CH_2$$
$$\phantom{O-CH_2-}OH\ \ OH$$

and corresponding structures with 1.2.dioleoylglycerol.

2) $R_1$: 1.2-dioleoylglycerol
   $R_2$: glycerol
   $R_3$: methyl $$CH_2-O-CO-(CH_2)_7-CH=CH-(CH_2)_7-CH_3$$
$$CH-O-CO-(CH_2)_7-CH=CH-(CH_2)_7-CH_3$$
$$CH_2\diagdown$$
$$O-\overset{O}{\underset{\|}{P}}-O-CH_2-CH-CH_2$$
$$O-CH_3\ \ \ \ \ OH\ \ OH$$

EXAMPLE 3

Liposomes of the composition

|  | Molar ratio |
| --- | --- |
| 1.2-Distearoyl-sn-glycero-3-phosphocholine | 40% |
| Cholesterol | 30% |
| Cholesterol-phospho-diglycerol | 20% |
| Cholesterol-phospho-glycerol, $Na^{(+)}$ salt | 10% |
|  | 100% | accumulate predominantly in the spleen, whereas liposomes of the usual composition e.g.

|  |  |
| --- | --- |
| 1.2-Distearoyl-sn-glycero-3-phosphocholine | 50% |
| Cholesterol | 40% |
| 1.2-Distearoyl-sn-glycero-3-phosphoglycerol, $Na^{(+)}$ salt | 10% |
|  | 100% |

The invention claimed is:

1. A compound of the formula (I)

$$R^1-O-\overset{\overset{O}{\|}}{\underset{\underset{R^3}{|}}{P}}-O-R^2$$

in which $R^1$ is a residue selected from cholesterol, diacyiglycerols, dialkyiglycerols, acylalkyiglycerols, ceramides, primary or secondary alcohols having 12 to 24 C atoms or acylglycerobenzyl ethers, and each of $R^2$ and $R^3$ is a residue independently selected from ethanolamine, N-methylethanolamine, propanolamine, choline, glycerol, oligoglycerols, glycoglycerols or serine, each of which may optionally comprise protective groups.

2. The compound as claimed in claim 1, characterized in that $R^1$ is a cholesterol residue.

3. The compound as claimed in claim 1, characterized in that $R^1$ is a 1-octadecyl-2-methyl-sn-glycerol residue.

4. The compound as claimed in claim 1, characterized in that $R^2$ is a glycerol residue.

5. The compound as claimed in claim 1, characterized in that $R^3$ is a glycerol residue.

6. The compound as claimed in claim 1, selected from cholesteryl-phospho-diglycerol, cholesteryl-phospho-glycerol-glyceroglycerol, cholesteryl-phospho-di-glycoglycerol, 1,2-dimyristoyl-sn-glycero-3-phospho-diglycerol, 1,2-dipalmitoyl-sn-glycero-3-phospho-diglycerol, 1,2-distearoyl-sn-glycero-3 -phospho-diglycerol, 1,2-dioleoyl-sn-glycero-3-phospho-diglycerol, 1,2-dioleoyl-sn-glycero-3-phospho-di-glycoglycerol, 1,2-dioleoyl-sn-glycero-3-phospho-di-glyceroglycerol.

7. A process for preparing a compound according to formula (I) as claimed in claim 1, characterized in that a compound of the formula (II)

$$R^1-O-\overset{\overset{O}{\|}}{\underset{\underset{O}{|}}{P}}-O-R^2$$

is esterified with a compound of the formula (III)
$HO-R^3$.

8. A liposome comprising a compound as claimed in claim 1.

9. A medicament comprising a compound as claimed in claim 1.

10. A medicament comprising a liposome as claimed in claim 8.

\* \* \* \* \*